(12) United States Patent
Faries, Jr. et al.

(10) Patent No.: US 7,611,504 B1
(45) Date of Patent: Nov. 3, 2009

(54) METHOD AND APPARATUS FOR FACILITATING INJECTION OF MEDICATION INTO AN INTRAVENOUS FLUID LINE WHILE MAINTAINING STERILITY OF INFUSED FLUIDS

(75) Inventors: Durward I. Faries, Jr., Las Vegas, NV (US); Bruce R. Heymann, Vienna, VA (US); David Hendrix, Ashburn, VA (US)

(73) Assignee: Patented Medical Solutions LLC, Las Vegas, NV (US)

( * ) Notice: Subject to any disclaimer, the term of this patent is extended or adjusted under 35 U.S.C. 154(b) by 345 days.

(21) Appl. No.: 10/795,333

(22) Filed: Mar. 9, 2004

(51) Int. Cl.
*A61M 25/18* (2006.01)

(52) U.S. Cl. .................. 604/539; 604/533; 604/534; 604/535; 604/538; 604/284; 604/113

(58) Field of Classification Search .................. 604/113, 604/167.01, 167.02, 167.04, 167.06, 244, 604/263, 533–535, 538, 539, 284, 114, 117, 604/162, 163, 171
See application file for complete search history.

(56) References Cited

U.S. PATENT DOCUMENTS

| | | | |
|---|---|---|---|
| 522,866 | A | 7/1894 | Weinhagen et al. |
| 558,979 | A | 4/1896 | Noble |
| 675,647 | A | 6/1901 | Andersen et al. |
| 785,524 | A | 3/1905 | Shea |
| 803,352 | A | 10/1905 | Meyer |
| 1,062,111 | A | 5/1913 | Nylander |
| 1,092,643 | A | 4/1914 | Goolsby |
| 1,110,919 | A | 9/1914 | Gamble |
| 1,223,274 | A | 4/1917 | Hallock |
| 1,390,500 | A | 9/1921 | Christian |

(Continued)

FOREIGN PATENT DOCUMENTS

DE 3709122 9/1988

(Continued)

OTHER PUBLICATIONS

"Luer Lock Males"; Minerve Polymeres; retrieved from the Internet Feb. 6, 2002: http://minerve-polymeres.com/males.html; 2 pages.

(Continued)

*Primary Examiner*—Kevin C Sirmons
*Assistant Examiner*—Laura C Schell
(74) *Attorney, Agent, or Firm*—Edell, Shapiro & Finnan, LLC

(57) ABSTRACT

A warming device for an IV fluid line according to the present invention includes a warmer unit and a wye type fitting with an injection site. The warmer unit includes a tube for intravenous fluid and channels containing a warming fluid to heat the IV tube. One fitting branch is connected to an intravenous fluid source, while the remaining branch houses the injection site. The injection site branch includes an injection safety member that ensures a syringe needle or other instrument is contained within the fitting to prevent rupture of the IV tube. The warming device may include an additional wye type fitting coupled to the initial fitting and including another injection site, where the fittings typically exclude the safety member. A syringe needle is inserted into the additional injection site to prevent rupture of the IV tube. In addition, the warming device may be configured for needleless injections.

12 Claims, 4 Drawing Sheets

U.S. PATENT DOCUMENTS

| | | |
|---|---|---|
| 1,479,451 A | 1/1924 | Buckstein |
| 1,493,450 A | 5/1924 | Richardson |
| 1,726,212 A | 8/1929 | Bucky |
| 1,770,832 A | 7/1930 | Bass |
| 1,794,215 A | 2/1931 | Titus |
| 1,838,026 A | 12/1931 | Williams |
| 1,847,954 A | 3/1932 | Fisher |
| 1,960,417 A | 5/1934 | Pain, Jr. |
| 1,982,213 A | 11/1934 | Hopkins |
| 1,987,119 A | 1/1935 | Long |
| 1,995,302 A | 3/1935 | Goldstein |
| 2,063,902 A | 12/1936 | Beasley |
| 2,087,586 A | 7/1937 | Tishman |
| 2,124,293 A | 7/1938 | Goldstein |
| 2,204,764 A | 6/1940 | Mayo |
| 2,254,994 A | 9/1941 | Butland |
| 2,470,481 A | 5/1949 | Freeman |
| 2,701,789 A | 2/1955 | White |
| 2,766,907 A | 10/1956 | Wallace, Jr. |
| 2,910,981 A * | 11/1959 | Wilson et. al. ............... 604/114 |
| 3,140,716 A | 7/1964 | Harrison et al. |
| 3,247,851 A | 4/1966 | Seibert |
| 3,293,868 A | 12/1966 | Gonzalez |
| 3,370,153 A | 2/1968 | Du Fresne et al. |
| 3,475,590 A | 10/1969 | Pins |
| 3,485,245 A | 12/1969 | Lahr et al. |
| 3,526,134 A | 9/1970 | Schaus |
| 3,551,641 A | 12/1970 | Truhan |
| 3,590,215 A | 6/1971 | Anderson et al. |
| 3,612,059 A | 10/1971 | Ersek |
| 3,614,385 A | 10/1971 | Horstmann |
| 3,629,552 A | 12/1971 | Edging |
| 3,636,767 A | 1/1972 | Duffy |
| 3,640,277 A | 2/1972 | Adelberg |
| 3,651,695 A | 3/1972 | Brown |
| 3,845,661 A | 11/1974 | Hollweck et al |
| 3,895,741 A | 7/1975 | Nugent |
| 3,908,652 A | 9/1975 | Weissinger |
| 4,009,615 A | 3/1977 | Ruhl |
| 4,038,519 A | 7/1977 | Foucras |
| 4,090,514 A | 5/1978 | Hinck et al. |
| 4,098,123 A | 7/1978 | Granzow, Jr. |
| 4,121,574 A | 10/1978 | Lester |
| 4,121,585 A | 10/1978 | Becker, Jr. |
| 4,138,890 A | 2/1979 | Brown |
| 4,167,663 A | 9/1979 | Granzow, Jr. et al. |
| 4,187,847 A | 2/1980 | Loeser |
| 4,293,762 A | 10/1981 | Ogawa |
| 4,309,592 A | 1/1982 | Le Boeuf |
| 4,329,569 A | 5/1982 | Hjortsberg et al. |
| 4,336,435 A | 6/1982 | Kashyap et al. |
| 4,356,383 A | 10/1982 | Dahlberg |
| 4,375,813 A | 3/1983 | Hessel |
| 4,384,578 A | 5/1983 | Winkler |
| 4,430,078 A | 2/1984 | Sprague |
| 4,464,563 A | 8/1984 | Jewett |
| 4,490,884 A | 1/1985 | Vickers |
| 4,495,402 A | 1/1985 | Burdick et al. |
| 4,523,078 A | 6/1985 | Lehmann |
| 4,531,941 A | 7/1985 | Zasuwa |
| 4,532,414 A | 7/1985 | Shah et al. |
| 4,543,095 A | 9/1985 | Jensen |
| 4,551,136 A | 11/1985 | Mandl |
| 4,585,435 A | 4/1986 | Vaillancourt |
| 4,585,441 A | 4/1986 | Archibald |
| 4,613,327 A | 9/1986 | Tegrarian et al. |
| 4,614,514 A | 9/1986 | Carr et al. |
| 4,625,086 A | 11/1986 | Karino |
| 4,626,243 A | 12/1986 | Singh et al. |
| 4,628,186 A | 12/1986 | Bergemann et al. |
| 4,634,432 A | 1/1987 | Kocak |
| 4,651,813 A | 3/1987 | Witt et al. |
| 4,657,004 A | 4/1987 | Coffey |
| 4,678,460 A | 7/1987 | Rosner |
| 4,680,445 A | 7/1987 | Ogawa |
| 4,682,979 A | 7/1987 | Girouard |
| 4,684,367 A | 8/1987 | Schaffer et al. |
| 4,705,505 A * | 11/1987 | Fried ........................ 604/80 |
| 4,707,587 A | 11/1987 | Greenblatt |
| 4,709,135 A | 11/1987 | Dietrich et al. |
| 4,735,609 A | 4/1988 | Comeau et al. |
| 4,745,248 A | 5/1988 | Hayes |
| 4,747,826 A | 5/1988 | Sassano |
| 4,756,299 A | 7/1988 | Podella |
| 4,759,749 A | 7/1988 | Verkaart |
| 4,772,778 A | 9/1988 | Ogawa |
| 4,781,548 A | 11/1988 | Alderson et al. |
| 4,782,212 A | 11/1988 | Bakke |
| 4,801,777 A | 1/1989 | Auerbach |
| 4,804,367 A | 2/1989 | Smith et al. |
| 4,808,159 A | 2/1989 | Wilson |
| 4,823,833 A | 4/1989 | Hogan et al. |
| 4,832,689 A | 5/1989 | Mauerer et al. |
| 4,844,074 A | 7/1989 | Kurucz |
| 4,847,470 A | 7/1989 | Bakke |
| 4,859,360 A | 8/1989 | Suzuki et al. |
| 4,874,033 A | 10/1989 | Chatelain et al. |
| 4,874,359 A | 10/1989 | White et al. |
| 4,878,537 A | 11/1989 | Verkaart |
| 4,900,308 A | 2/1990 | Verkaart |
| 4,906,816 A | 3/1990 | van Leerdam |
| 4,923,681 A | 5/1990 | Cox et al. |
| 4,934,336 A | 6/1990 | White |
| 5,013,889 A | 5/1991 | Bakke |
| 5,019,047 A | 5/1991 | Kriesel |
| 5,042,455 A | 8/1991 | Yue et al. |
| 5,059,182 A | 10/1991 | Laing |
| 5,061,241 A | 10/1991 | Stephens, Jr. et al. |
| 5,061,630 A | 10/1991 | Knoopf et al. |
| 5,063,994 A | 11/1991 | Verkaart |
| 5,073,167 A | 12/1991 | Carr et al. |
| 5,075,167 A | 12/1991 | Yamauchi et al. |
| 5,081,697 A | 1/1992 | Manella |
| 5,096,822 A | 3/1992 | Rosenkrans, Jr. et al. |
| 5,097,898 A | 3/1992 | Verkaart |
| 5,106,373 A | 4/1992 | Augustine et al. |
| 5,108,372 A | 4/1992 | Swenson |
| 5,125,069 A | 6/1992 | O'Boyle |
| 5,125,900 A | 6/1992 | Teves |
| 5,129,033 A | 7/1992 | Ferrara et al. |
| 5,169,389 A | 12/1992 | Kriesel |
| 5,180,896 A | 1/1993 | Gibby et al. |
| 5,184,613 A | 2/1993 | Mintz |
| 5,186,057 A | 2/1993 | Everhart |
| 5,195,976 A | 3/1993 | Swenson |
| 5,205,820 A | 4/1993 | Kriesel |
| 5,211,631 A | 5/1993 | Sheaff |
| 5,232,439 A | 8/1993 | Campbell et al. |
| 5,241,951 A | 9/1993 | Mason et al. |
| 5,243,833 A | 9/1993 | Coelho et al. |
| 5,245,693 A | 9/1993 | Ford et al. |
| 5,250,032 A | 10/1993 | Carter, Jr. et al. |
| 5,254,094 A | 10/1993 | Starkey et al. |
| 5,261,411 A | 11/1993 | Hughes |
| 5,261,875 A | 11/1993 | Spears et al. |
| 5,263,323 A | 11/1993 | Maus et al. |
| 5,263,929 A | 11/1993 | Falcone et al. |
| 5,279,558 A | 1/1994 | Kriesel |
| 5,279,598 A | 1/1994 | Sheaff |
| 5,282,264 A | 1/1994 | Reeves et al. |
| 5,290,222 A | 3/1994 | Feng et al. |
| 5,290,230 A | 3/1994 | Ainsworth et al. |
| 5,297,234 A | 3/1994 | Harms et al. |
| 5,308,335 A | 5/1994 | Ross et al. |

| | | | | | |
|---|---|---|---|---|---|
| 5,318,540 A | 6/1994 | Athayde et al. | 5,928,196 A | 7/1999 | Johnson et al. |
| 5,330,431 A | 7/1994 | Herskowitz | 5,935,099 A | 8/1999 | Peterson et al. |
| 5,338,157 A | 8/1994 | Blomquist | 5,935,106 A | 8/1999 | Olsen |
| 5,342,313 A | 8/1994 | Campbell et al. | 5,954,485 A | 9/1999 | Johnson et al. |
| 5,348,539 A | 9/1994 | Herskowitz | 5,961,492 A | 10/1999 | Kriesel et al. |
| 5,364,371 A * | 11/1994 | Kamen .................. 604/251 | 5,961,700 A | 10/1999 | Oliver |
| 5,364,385 A | 11/1994 | Harms et al. | 5,989,238 A | 11/1999 | Ginsburg |
| 5,370,674 A | 12/1994 | Farrell | 6,024,539 A | 2/2000 | Blomquist |
| 5,381,510 A | 1/1995 | Ford et al. | 6,035,102 A | 3/2000 | Bakke |
| 5,389,078 A | 2/1995 | Zalesky et al. | 6,039,926 A | 3/2000 | Goldman |
| 5,397,875 A | 3/1995 | Bechtold, Jr. | 6,045,648 A | 4/2000 | Palmgren et al. |
| 5,399,166 A | 3/1995 | Laing | 6,062,429 A | 5/2000 | West et al. |
| 5,408,576 A | 4/1995 | Bishop | 6,096,007 A | 8/2000 | Haan et al. |
| 5,408,577 A | 4/1995 | Weber, Jr. et al. | 6,117,122 A | 9/2000 | Din et al. |
| 5,411,480 A | 5/1995 | Kriesel | 6,129,702 A | 10/2000 | Woias et al. |
| 5,411,482 A | 5/1995 | Campbell | 6,139,528 A | 10/2000 | Kistner et al. |
| 5,417,274 A | 5/1995 | Verkaart | 6,142,974 A | 11/2000 | Kistner et al. |
| 5,420,962 A | 5/1995 | Bakke | 6,146,359 A | 11/2000 | Carr et al. |
| 5,423,759 A | 6/1995 | Campbell | 6,146,362 A | 11/2000 | Turnbull et al. |
| 5,433,704 A | 7/1995 | Ross et al. | 6,174,300 B1 | 1/2001 | Kriesel et al. |
| 5,451,209 A | 9/1995 | Ainsworth et al. | 6,175,688 B1 | 1/2001 | Cassidy et al. |
| 5,474,538 A | 12/1995 | Stihler et al. | 6,221,045 B1 | 4/2001 | Duchon et al. |
| 5,485,408 A | 1/1996 | Blomquist | 6,221,051 B1 | 4/2001 | Hjertman et al. |
| 5,492,534 A | 2/1996 | Athayde et al. | 6,236,809 B1 | 5/2001 | Cassidy et al. |
| 5,512,043 A | 4/1996 | Verkaart | 6,254,572 B1 | 7/2001 | Knipfer et al. |
| 5,514,095 A | 5/1996 | Brightbill et al. | 6,261,261 B1 | 7/2001 | Gordon |
| 5,531,697 A | 7/1996 | Olsen et al. | 6,316,750 B1 | 11/2001 | Levin |
| 5,531,698 A | 7/1996 | Olsen | 6,334,707 B1 | 1/2002 | Ku |
| 5,538,399 A | 7/1996 | Johnson | 6,344,033 B1 | 2/2002 | Jepson et al. |
| 5,540,561 A | 7/1996 | Johnson | 6,467,953 B1 | 10/2002 | Faries, Jr. et al. |
| 5,564,915 A | 10/1996 | Johnson | 6,480,257 B2 | 11/2002 | Cassidy et al. |
| 5,567,119 A | 10/1996 | Johnson | 6,524,239 B1 | 2/2003 | Reed et al. |
| 5,567,136 A | 10/1996 | Johnson | 6,553,336 B1 | 4/2003 | Johnson et al. |
| 5,572,873 A | 11/1996 | Lavigne et al. | 6,566,631 B2 | 5/2003 | Faries, Jr. et al. |
| 5,573,516 A | 11/1996 | Tyner | 6,660,974 B2 | 12/2003 | Faries, Jr. et al. |
| 5,584,811 A | 12/1996 | Ross et al. | 6,722,782 B2 | 4/2004 | Faries, Jr. et al. |
| 5,590,648 A | 1/1997 | Mitchell et al. | 6,736,788 B1 | 5/2004 | Mongomery et al. |
| RE35,501 E | 5/1997 | Ross et al. | 6,748,164 B1 | 6/2004 | Kuzyk |
| 5,647,854 A | 7/1997 | Olsen et al. | 6,768,085 B2 | 7/2004 | Faries, Jr. et al. |
| 5,649,910 A | 7/1997 | Kriesel et al. | 6,824,528 B1 | 11/2004 | Faries, Jr. et al. |
| 5,658,250 A | 8/1997 | Blomquist et al. | 6,850,252 B1 | 2/2005 | Hoffberg |
| 5,658,252 A | 8/1997 | Johnson | 6,869,538 B2 | 3/2005 | Yu et al. |
| 5,662,611 A | 9/1997 | Beiser et al. | RE39,075 E | 4/2006 | Verkaart |
| 5,669,877 A | 9/1997 | Blomquist | 7,031,602 B2 | 4/2006 | Faries, Jr. et al. |
| 5,681,284 A | 10/1997 | Herskowitz | 7,031,778 B2 | 4/2006 | Hsiung et al. |
| 5,683,381 A | 11/1997 | Carr et al. | 7,041,941 B2 | 5/2006 | Faries, Jr. et al. |
| 5,690,614 A | 11/1997 | Carr et al. | 7,090,658 B2 | 8/2006 | Faries, Jr. et al. |
| 5,695,473 A | 12/1997 | Olsen | 7,176,030 B2 | 2/2007 | Fairies, Jr., et al. |
| 5,707,151 A | 1/1998 | Parker et al. | 7,307,245 B2 | 12/2007 | Faries, Jr. et al. |
| 5,707,431 A | 1/1998 | Verkaart et al. | 7,326,882 B2 | 2/2008 | Faries, Jr. et al. |
| 5,713,864 A | 2/1998 | Verkaart | 7,417,205 B2 | 8/2008 | Faries, Jr. et al. |
| 5,720,728 A | 2/1998 | Ford | 2002/0041621 A1 | 4/2002 | Faries, Jr. et al. |
| 5,729,653 A | 3/1998 | Magliochetti et al. | 2002/0156451 A1 | 10/2002 | Lenker |
| 5,733,263 A | 3/1998 | Wheatman | 2003/0114795 A1 | 6/2003 | Faries, Jr. et al. |
| 5,743,878 A | 4/1998 | Ross et al. | 2003/0216831 A1 | 11/2003 | Hart et al. |
| 5,755,275 A | 5/1998 | Rose et al. | 2003/0222933 A1 | 12/2003 | Choi |
| 5,772,409 A | 6/1998 | Johnson | 2003/0231990 A1 | 12/2003 | Faries, Jr. et al. |
| 5,788,669 A | 8/1998 | Peterson | 2004/0170409 A1 | 9/2004 | Faries, Jr. et al. |
| 5,788,671 A | 8/1998 | Johnson | 2005/0070845 A1 | 3/2005 | Faries, Jr. et al. |
| 5,806,528 A | 9/1998 | Magliochetti | 2005/0142013 A1 | 6/2005 | Faries, Jr. et al. |
| 5,807,332 A | 9/1998 | Augustine et al. | 2005/0222933 A1 | 10/2005 | Wesby |
| 5,810,771 A | 9/1998 | Blomquist | 2006/0020255 A1 | 1/2006 | Cassidy et al. |
| 5,823,746 A | 10/1998 | Johnson | 2006/0253075 A1 | 11/2006 | Faries, Jr. et al. |
| 5,824,000 A | 10/1998 | Pavlo et al. | 2007/0000910 A1 | 1/2007 | Faries, Jr. et al. |
| 5,829,880 A | 11/1998 | Diedrich | 2007/0106243 A1 | 5/2007 | Faries, Jr. et al. |
| 5,840,068 A | 11/1998 | Cartledge | 2007/0161952 A1 | 7/2007 | Faries, Jr. et al. |
| 5,875,282 A | 2/1999 | Jordan | 2007/0215018 A1 | 9/2007 | Faries, Jr. et al. |
| 5,876,370 A | 3/1999 | Blomquist | 2008/0147016 A1 | 6/2008 | Faries et al. |
| 5,879,143 A | 3/1999 | Cote et al. | 2008/0205481 A1 | 8/2008 | Faries et al. |
| 5,879,329 A | 3/1999 | Ginsburg | | | |
| 5,891,096 A | 4/1999 | Hyun et al. | | FOREIGN PATENT DOCUMENTS | |
| 5,893,843 A | 4/1999 | Rodrigues | | | |
| 5,919,218 A | 7/1999 | Carr | FR | 2711393 | 4/1995 |

| | | |
|---|---|---|
| FR | 2786057 | 5/2000 |
| GB | 2029677 A | 3/1980 |
| WO | WO 98/38953 | 9/1998 |
| WO | WO 99/22786 | 5/1999 |
| WO | WO 99/26690 | 6/1999 |
| WO | WO 99/58177 | 11/1999 |

OTHER PUBLICATIONS

"Luer Lock Femelles"; Minerve Polymeres; retrieved from the Internet Feb. 6, 2002: http://minerve-polymers.com/femelles.html; 2 pages.

"Needleless Access Connector (Retrograde Free)"; NAC Plus; Kipp Med; 1 page.

"HOTLINE Disposables"; retrieved from the Internet Feb. 4, 2002: www.simslevell.com/hldisp.htm; 3 pages.

"I.V. Systems"; Life-Assist, Inc.; retrieved for the Internet Dec. 17, 2001; www.life-assist.com/iv/iv.html; 3 pages.

"NAC PRN version: Needleless Access Connector"; Porex Medical Products Group; retrieved from the Internet Mar. 6, 2002: www.porex.com/english/medical/mnac.asp; 1 page.

"HOTLINE Eliminates Patient Line Cool-Down"; retrieved from the Internet Jan. 18, 2002: www.simslevell.com/hotln2.htm; 5 pages.

*Health Devices*, vol. 25, No. 10, Oct. 1996.

Minco Products, Inc., *Bulletin CTI98*. 1996.

Eurotherm Controls, Inc., *Model 2116 Temperature Controller*, 1997.

Ellenwood, *Drop Detector*, IBM Technical Bulletin, vol. 12, No. 5, Oct. 1969.

CBi Medical, Inc., *IV Fluid Warmer Model 8362*, 1992.

\* cited by examiner

METHOD AND APPARATUS FOR FACILITATING INJECTION OF MEDICATION INTO AN INTRAVENOUS FLUID LINE WHILE MAINTAINING STERILITY OF INFUSED FLUIDS

BACKGROUND OF THE INVENTION

1. Technical Field

The present invention pertains to infusion devices that enable injection of fluids into an intravenous fluid line during infusion of intravenous solution into a patient. In particular, the present invention is directed toward an infusion warming device for warming infused fluids within a fluid line and including an injection site to facilitate injection of medicaments into the fluid line without compromising infused fluid sterility.

2. Discussion of Related Art

Intravenous (IV) fluids are typically infused into a patient utilizing a liquid-filled bag or container and an IV fluid line. The fluids are generally delivered from the container to the patient via gravitational forces and/or applied pressure. It is important in many situations that the temperature of the intravenous fluid be maintained within a desirable and safe temperature range upon entering the patient body so as to eliminate any potential for thermal shock and injury to the patient.

Accordingly, the related art provides various devices for controlling the temperature of fluid in an IV line for infusion into a patient. One such device employs a heat exchanger to heat and maintain fluid flowing within an IV line at a desired temperature. For example, U.S. Pat. No. 5,063,994 (Verkaart) discloses a heat exchanger including a central tube for carrying an infusate and two outer channels for carrying a heat exchange fluid. A first channel carries the heat exchange fluid from an inlet end to an opposite end, while a second channel returns the fluid to the inlet end. An end cap at the inlet end is connected to a source of heat exchange fluid and communicates with the channels. An end cap at the opposite end receives the heat exchange fluid from the first channel and re-directs the fluid to the second channel. The end caps have connectors for facilitating connection with lines from an infusate source and a patient.

In addition, it may be beneficial or required in certain situations to administer medications or medicaments in combination with IV fluids via the fluid line. Although the Verkaart device warms fluid, there is no provision for enabling administration of medicaments within the fluid. The related art has attempted to overcome this problem by providing infusion warming devices enabling injection of medicaments into an IV line. This is typically accomplished by inserting a syringe needle into a line injection site. For example, the HOTLINE device, available from SIMS Level 1, Inc., includes a heat exchanger employing a layer of circulating warm water surrounding an IV line in order to heat intravenous fluid flowing therein. The device further includes an injection site for receiving a syringe needle. The injection site includes a membrane or seal to accommodate insertion and removal of the syringe needle within that site.

However, this type of device suffers from several disadvantages. In particular, the injection site generally enables syringe needles to compromise intravenous fluid sterility. Specifically, a syringe needle may be inserted within and extend through the injection site, thereby contacting and inadvertently puncturing the IV line. This results in mixing of IV fluid with the surrounding warm water and compromises IV fluid sterility. As a consequence, the patient may suffer adverse affects, including infections and/or illness. In addition, the non-sterile conditions may compromise performance of a medical procedure and/or facilitate extended hospital stays for the patient, thereby substantially increasing medical costs.

OBJECTS AND SUMMARY OF THE INVENTION

Accordingly, it is an object of the present invention to facilitate injection of medicaments into an IV line without comprising sterility of IV fluid flowing therein.

It is another object of the present invention to facilitate injection of medicaments into an IV line without compromising IV fluid sterility by configuring an injection site of a line warming device to prevent puncturing of the IV line by a syringe needle during an injection.

Yet another object of the present invention is to facilitate injection of medicaments into an IV line without compromising IV fluid sterility by employing a needleless injection site with an IV line warming device.

The aforesaid objects may be achieved individually and/or in combination, and it is not intended that the present invention be construed as requiring two or more of the objects to be combined unless expressly required by the claims attached hereto.

According to the present invention, a warming device for an IV fluid line includes a warmer or heat transfer unit and a fitting including an injection site to receive a syringe needle. The warmer unit includes a tube for intravenous (IV) fluid and channels encompassing the tube for containing a warming or heat transfer fluid to heat the IV fluid tube. A first channel directs the heat transfer fluid along the IV tube and away from a heat transfer fluid inlet, while a second channel directs the heat transfer fluid back toward the inlet to a heat transfer fluid outlet. An end cap at the warmer unit proximal end is connected to a source of heat transfer fluid, while another end cap at the warmer unit distal end directs the heat transfer fluid from the first channel to the second channel.

The proximal and distal end caps are coupled to the fitting and a line to a patient, respectively. The fitting is attached to the proximal end cap and includes a wye type configuration. One fitting branch is connected to an intravenous fluid source, while the remaining branch houses the injection site. The injection site branch includes an injection safety member that ensures a syringe needle or other instrument is properly contained within the fitting to prevent rupture of the IV tube and contamination of intravenous fluid flowing therein. The warming device may alternatively include an additional wye type fitting. The additional fitting is coupled to the initial warming device fitting and includes another injection site. The warming device fittings typically exclude the injection safety member, where a syringe needle is inserted into the additional fitting injection site to prevent rupture of the IV tube by the syringe needle.

In addition, the warming device may be configured for needleless injections. Specifically, an injection site branch of the warming device fitting includes a connection member in the form of a female Luer connector. The connection member enables engagement of the fitting with a needleless connector that facilitates needleless injections into the IV line, thereby preventing rupture of the IV tube.

The above and still further objects, features and advantages of the present invention will become apparent upon consideration of the following detailed description of specific embodiments thereof, particularly when taken in conjunction

DETAILED DESCRIPTION OF THE PREFERRED EMBODIMENTS

Figure 1:
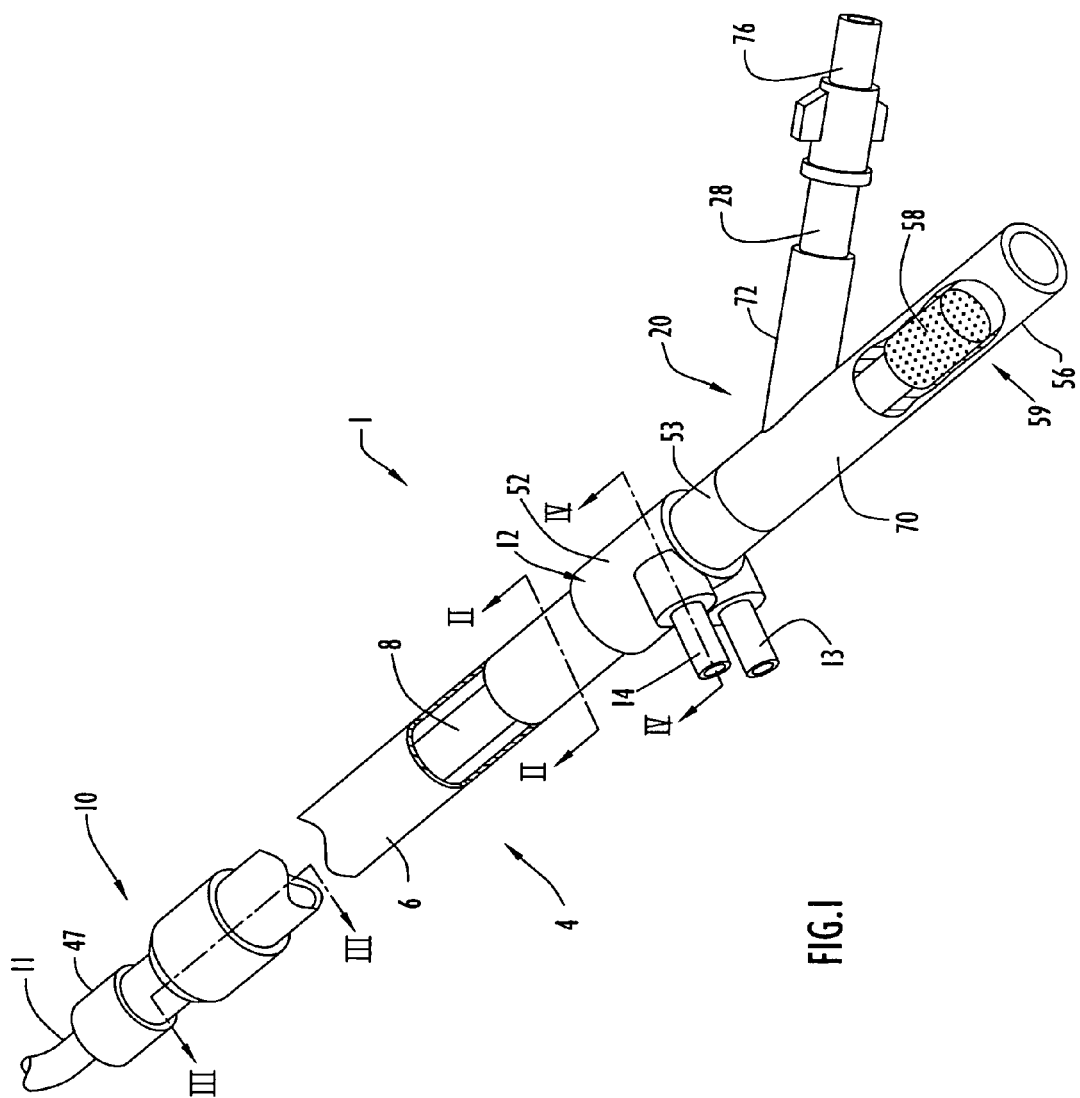
FIG. 1 is a perspective view in partial section of a warming device attached to an IV line and including an injection site configured to maintain fluid sterility during injections according to the present invention.
Figure 2:
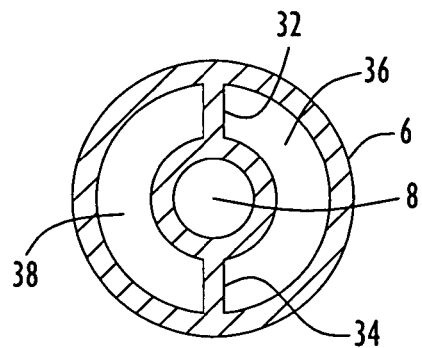
FIG. 2 is a view in elevation and section of the warming device of FIG. 1 taken along lines II-II.

A warming device or system according to the present invention for maintaining IV fluids flowing within an IV line at a selected temperature and ensuring sterility of the fluids during injections is illustrated in FIGS. 1-2. Specifically, warming system 1 includes a heat transfer or warmer unit 4 and a wye type fitting 20 that includes an injection site 59 for receiving a syringe needle or other instrument. Warmer unit 4 includes a generally cylindrical IV tube 8 disposed within a generally cylindrical heat transfer tube 6. The tubes are disposed in a substantially concentric fashion with IV tube 8 extending longitudinally for substantially the entire length of heat transfer tube 6. A distal end cap 10 is attached to a distal end of heat transfer tube 6 and connects in a suitable manner, via a male Luer fitting or connector 47, to an IV line portion 11 that extends to an infusion site (not shown) on a patient body (e.g., arm or other suitable location).

The area between IV tube 8 and heat transfer tube 6 receives a warming or heat transfer fluid, while IV tube 8 contains intravenous fluid for the patient. The heat transfer fluid flows within the area to heat the intravenous fluid flowing within tube 8. Walls 32, 34 extend between the IV and heat transfer tubes and are angularly displaced from each other by approximately one-hundred eighty degrees relative to the IV tube. The walls partition the area into channels 36, 38 for containing the heat transfer fluid. Channel 36 directs the heat transfer fluid distally along tube 8 and away from a heat transfer fluid inlet 13, while channel 38 directs the fluid proximally along the IV tube to a heat transfer fluid outlet 14. The fluid in channel 36 is directed into channel 38 via distal end cap 10 secured to the distal ends of tubes 6, 8. Inlet 13 and outlet 14 are each connected to a heat transfer fluid supply source (not shown) that maintains the heat exchange fluid at a particular temperature. For an example of a type of heated fluid source that may be utilized with the present invention, reference is made to U.S. Pat. No. 4,759,749 (Verkaart), the disclosure of which is incorporated herein by reference in its entirety.

Figure 3:
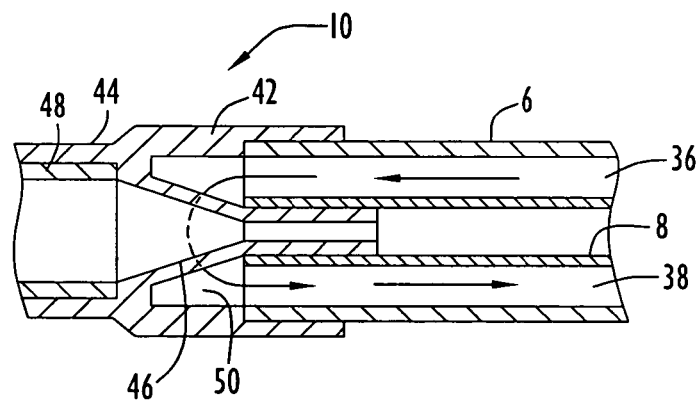
FIG. 3 is a view in partial section of a distal end cap of the warming device of FIG. 1 taken along lines III-III.

Referring to FIG. 3, distal end cap 10 includes a generally cylindrical tube engagement member 42, a generally cylindrical connector member 44 and a conduit 46. Engagement member 42 engages the outer surface of heat transfer tube 6. Conduit 46 is defined in the engagement member bottom wall and tapers in dimension therefrom to be received in IV tube 8. Male Luer fitting 47 (FIG. 1) includes a projection 48 that is received in connector member 44, thereby placing the Luer fitting in fluid communication with conduit 46. The area between conduit 46 and engagement member 42 forms a chamber 50 for redirecting heat transfer fluid from channel 36 into channel 38. The Luer fitting is connected to line portion 11 (FIG. 1) and enables delivery of heated IV fluid from warmer unit 4 to the patient.

Figure 4:
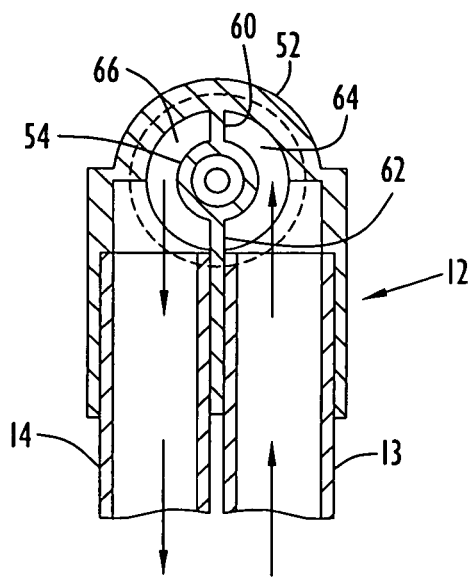
FIG. 4 is a view in partial section of a proximal end cap of the warming device of FIG. 1 taken along lines IV-IV.

Referring to FIG. 4, a proximal end cap 12, similar to end cap 10, is disposed toward the warmer unit proximal end. Specifically, the proximal end cap includes a generally cylindrical tube engagement member 52, a generally cylindrical connector member 53 (FIG. 1) and a conduit 54 each substantially similar to the corresponding components described above for end cap 10. Engagement member 52 engages the outer surface of heat transfer tube 6. Conduit 54 is defined in an engagement member bottom wall and tapers in dimension therefrom to be received in IV tube 8 as described above. End cap 12 further includes walls 60, 62 that are aligned with walls 32, 34 of heat transfer tube 6 to enable fluid to flow between end cap 12 and appropriate channels 36, 38. Walls 60, 62 basically partition the area between engagement member 52 and conduit 54 to form inlet and outlet chambers 64, 66 that align with channels 36, 38. In other words, walls 60, 62 isolate fluid flowing within the proximal end cap and channels and enable fluid from channel 38 to enter outlet 14 and fluid from inlet 13 to enter channel 36. End cap 12 further includes inlet 13 and outlet 14 extending transversely therefrom to connect with a heat transfer fluid supply source (not shown). The heat transfer fluid enters the warmer unit via inlet 13 and travels within channel 36 to distal end cap 10 and returns via channel 38 to exit the warmer unit via outlet 14. A continuous supply of heat transfer fluid is delivered from the fluid supply source to the warmer unit to surround and heat fluid within IV tube 8, while the warmer unit configuration maintains separation between the transfer and IV fluid flowing within heat transfer tube 6. For an example of the structure and operation of this type of warmer unit, reference is made to U.S. Pat. No. 5,063, 994 (Verkaart), the disclosure of which is incorporated herein by reference in its entirety.

Referring back to FIG. 1, warming device 1 includes wye type fitting 20 attached to the proximal end of end cap 12 and in fluid communication with conduit 54. The fitting includes a generally cylindrical base 70 with a substantially cylindrical projection 72 and an injection safety member 56. The projection extends from a base distal portion and is typically oriented at an approximate forty-five degree angle relative to a base longitudinal axis. An IV line portion 28 is connected to the projection and typically extends to an IV fluid source. A female Luer connector 76 is typically disposed at the line portion proximal end to facilitate connection of the line to the source.

The base proximal portion includes injection site 59 to enable injection of medicaments or other fluids into the IV line. The injection site resides at the proximal end of the base and preferably includes a membrane 58 to seal the base proximal end and maintain fluids within the fitting. The membrane further enables insertion and removal of a syringe needle within the fitting for injection of medicaments. The membrane may be implemented by a cap or plug that maintains a fluid tight seal and permits removable insertion of the syringe needle. For an example of the structure and operation of a fitting injection site, reference is made to U.S. Pat. No. 4,585, 435 (Vaillancourt), the disclosure of which is incorporated herein by reference in its entirety. Since syringes typically include needles having maximum length dimensions in the approximate range of 2.5 to 3.0 inches, the needles tend to extend beyond of the confines of the base (e.g., typically including a length dimension of approximately two inches) and contact and rupture IV tube 8. This enables the IV fluid to mix with the non-sterile heat transfer fluid, thereby compromising sterility of the IV fluid and/or contaminating a medical procedure. In order to ensure sterility of the IV fluid during injections, base 70 includes injection safety member 56 disposed at the proximal end of the injection site. The safety member is substantially cylindrical and includes an open proximal end and a hollow interior to receive a syringe needle or other medical instrument. The safety member width dimensions are similar to those of base 70 (e.g., less than those of a syringe body but greater than those of a syringe needle), while the safety member length dimensions provide the fitting with a length greater than that of the syringe needle. By way of example only, the safety member may include a length in the approximate range of 0.5 to 1.0 inches. The safety member basically serves as a stop to limit syringe needle insertion and prevent contact between the needle and IV tube 8. In other words, the safety member includes width and length dimensions sufficient to maintain the syringe needle within fitting 20. The syringe may contain and inject any medicaments or other fluids into the fitting to mix with IV fluid. The safety member may be attached to the base injection site branch via any suitable connectors or be formed integral with that branch. Alternatively, the base injection site branch may include elongated dimensions sufficient to maintain the syringe needle within the fitting as described above, or may include membrane 58 disposed at the proximal end of the safety member.

In operation, IV fluid is directed from an IV fluid source through IV line portion 28 to projection 72 of wye fitting 20. The IV fluid continues traveling through the fitting emerging at the base distal end and passing through end cap 12 into IV tube 8 of warmer unit 4. Heat transfer fluid is continuously circulated through the warmer unit via inlet 13, outlet 14, and channels 36, 38 as described above. The heat transfer fluid basically flows from a heat transfer fluid supply source and through warmer unit 4 to surround IV tube 8 and heat IV fluid flowing therein. The IV fluid passes through the IV tube and exits the warmer unit through distal end cap 10 into IV line portion 11 that extends to the infusion site. At any time during system operation, a syringe needle may be inserted into membrane 58 of fitting 20 to inject appropriate medicaments into the IV line. The medicaments mix with the IV fluid flowing within fitting 20 and toward the infusion site as described above. The safety member retains the syringe needle within the fitting to prevent the needle from contacting and rupturing the IV tube, thereby ensuring sterility of the IV fluid during injections.

Figure 5:
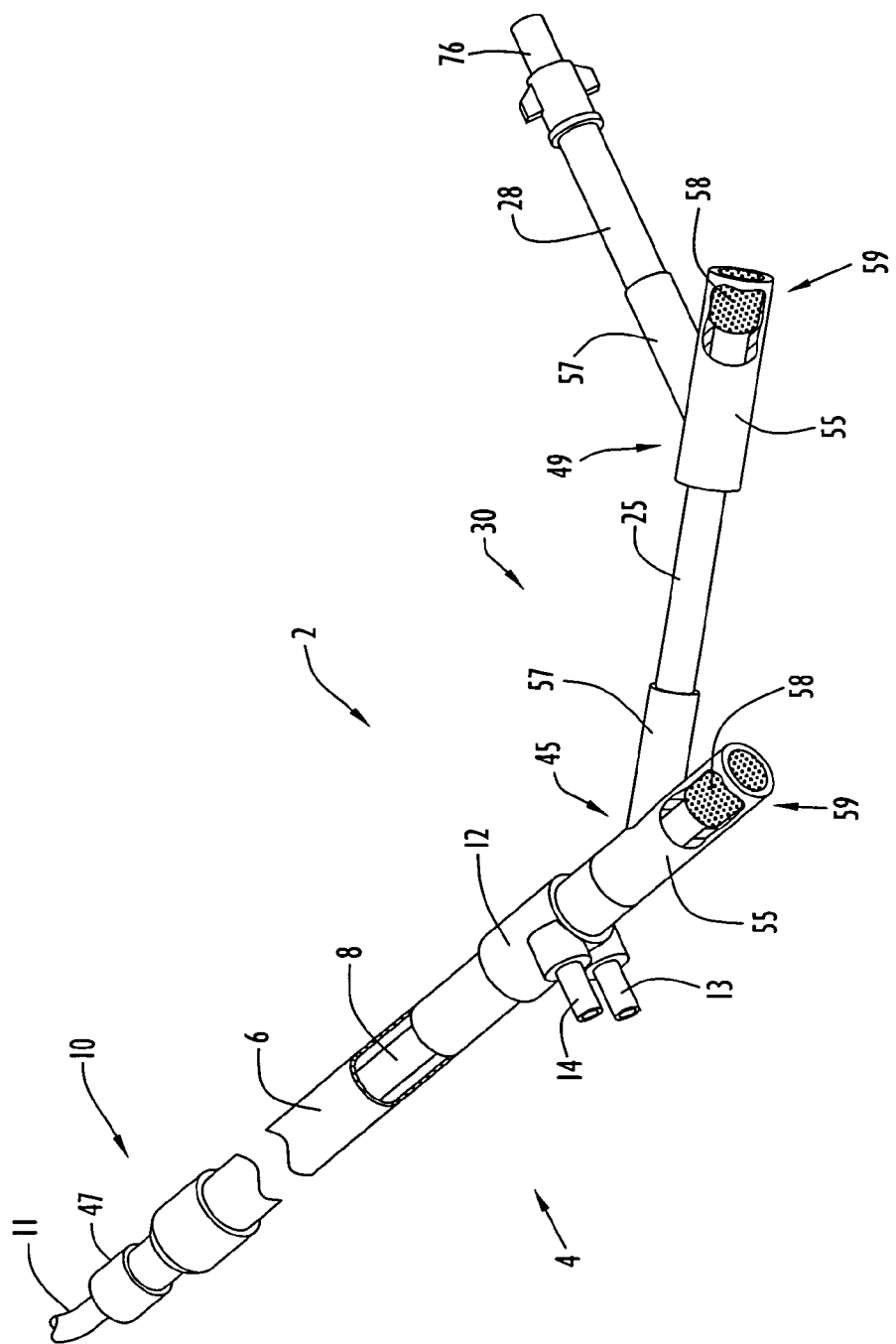
FIG. 5 is a perspective view in partial section of a warming device employing an additional fitting to maintain fluid sterility during injections according to the present invention.

An alternative embodiment of the warming device of the present invention is illustrated in FIG. 5. Specifically, device 2 includes a warmer unit 4 and a fitting assembly 30. The warmer unit is substantially similar to the warmer unit described above and includes IV tube 8 disposed within heat transfer tube 6 and distal and proximal end caps 10, 12. The area between the IV and heat transfer tubes receives a warming or heat transfer fluid, while IV tube 8 contains intravenous fluid for the patient as described above. The IV and heat transfer tubes are connected by walls that partition the area into channels for directing heat transfer fluid flow through the warmer unit in substantially the same manner described above. End cap 10 disposed at the warmer unit distal end is coupled to IV line portion 11 extending to the patient. Distal end cap 10 enables IV fluid to flow from IV tube 8 to IV line portion 11 and directs heat transfer fluid between the warmer unit channels as described above. Proximal end cap 12 is disposed at the warmer unit proximal end and includes fluid inlet 13 and fluid outlet 14. The proximal end cap facilitates flow of heat transfer fluid to and from a heated fluid supply source and through the appropriate channels as described above. The proximal end cap further enables IV fluid to flow into the IV tube as described above.

Fitting assembly 30 includes wye type fittings 45, 49 in fluid communication with each other to facilitate delivery of IV fluid from a source to the warmer unit. Fitting 45 is similar to fitting 20 described above and includes a generally cylindrical base 55 with substantially cylindrical projection 57. The projection extends from a base distal portion and is typically oriented at an approximate forty-five degree angle relative to a base longitudinal axis. The projection is connected to an IV line portion 25 that extends to wye type fitting 49. The base proximal portion includes injection site 59 to enable injection of medicaments or other fluids into the IV line. The injection site is substantially similar to the injection site described above and includes membrane 58 to seal the base proximal end and maintain fluids within the fitting. The membrane further enables insertion and removal of a syringe needle within the fitting for injection of medicaments.

As described above, syringes typically include needles having dimensions that enable the needle to extend beyond the base confines and contact and rupture IV tube 8, thereby compromising sterility of the IV fluid and/or contaminating a medical procedure. In order to ensure sterility of the IV fluid, wye type fitting 49 is employed to serve as the injection site and displace the syringe needle from the IV tube. Specifically, wye type fitting 49 is substantially similar to fitting 45 and includes base 55 and projection 57 each as described above. The base portion distal end is attached to IV line portion 25, while the proximal end includes an injection site 59 with membrane 58 as described above. The membrane basically seals the base proximal end and maintains fluids within the fitting. The membrane further enables insertion and removal of a syringe needle within the fitting for injection of medicaments as described above. The projection of fitting 49 is connected to an IV line portion 28 that extends to an IV fluid source. Female Luer connector 76 is typically disposed at the line portion proximal end to facilitate connection of the line to the source. Thus, IV fluid from the source flows through fittings 49 and 45 and warmer unit 4 to the patient. Medicaments are injected into the IV line via injection site 59 of fitting 49 in order to prevent the syringe needle from contacting and rupturing IV tube 8. Further, fitting 49 may be placed at any suitable location along the line to prevent rupture of the IV tube. Alternatively, fitting 45 may be utilized without fitting 49 and may be placed at any suitable location along the IV line to prevent a syringe needle from contacting and rupturing IV line 8. The warming unit and fittings may be connected in any fashion, or may be formed as an integral device for infusion of fluids.

In operation, IV fluid is directed from an IV fluid source through IV line portion 28 to projection 57 of fitting 49. The IV fluid flows through fitting 49 and into IV line portion 25 from the fitting base. Projection 57 of fitting 45 directs the IV fluid through proximal end cap 12 into IV tube 8. Heat transfer fluid is continuously circulated through warmer unit 4 to heat the IV fluid flowing in IV tube 8 as described above. The IV fluid passes through the IV tube and exits the warmer unit through distal end cap 10 into IV line portion 11 that extends to the infusion site. A syringe needle is preferably inserted into injection site 59 of fitting 49 to inject appropriate medicaments into the IV line. The medicaments mix with the IV fluid flowing within fitting 49 and flow through fitting 45 and warmer unit 4 toward the infusion site as described above. The displacement of the injection site within fitting 49 prevents the syringe needle from contacting and rupturing IV tube 8, thereby maintaining sterility of the IV fluid.

Figure 6:
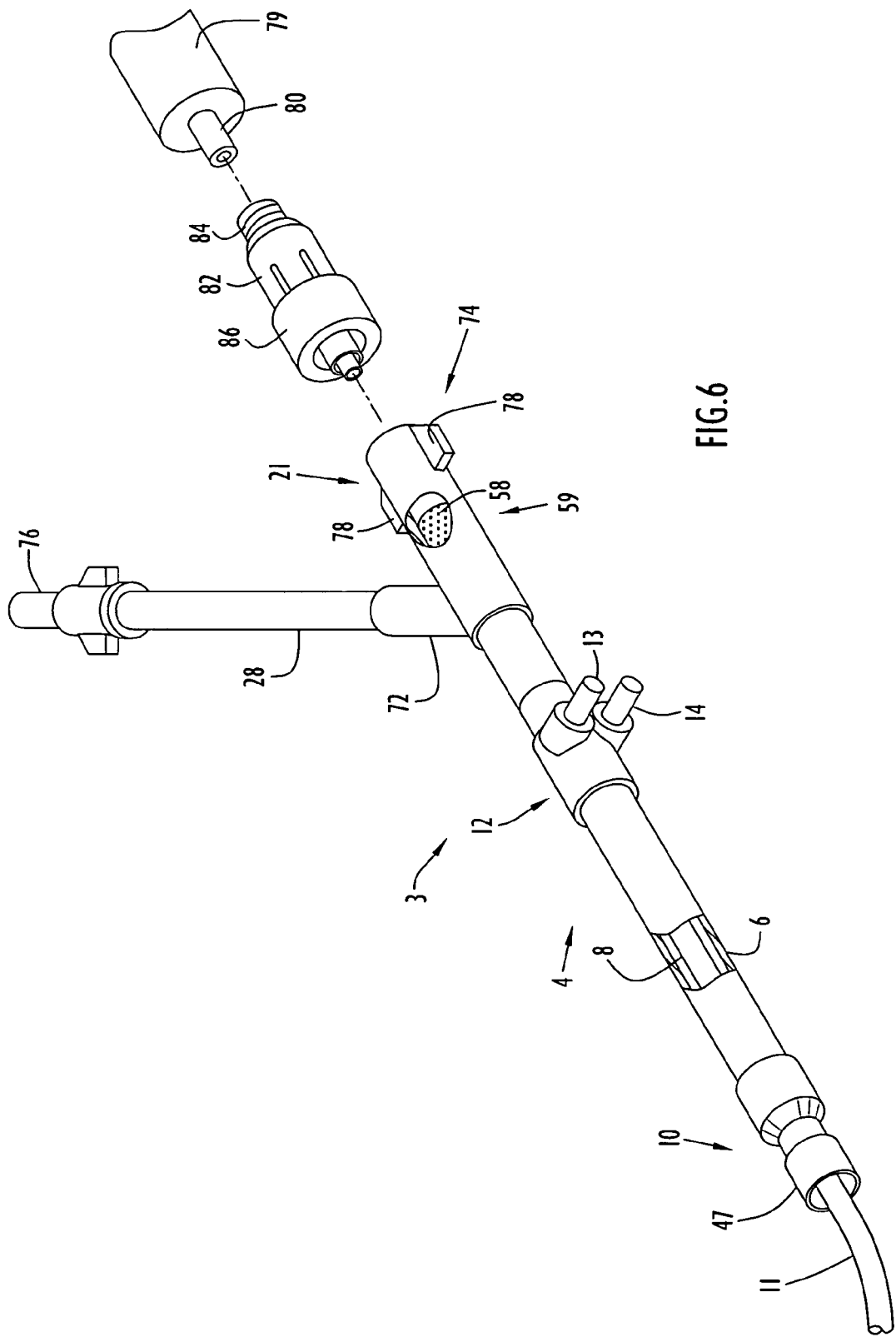
FIG. 6 is an exploded perspective view in partial section of a warming device configured for needleless injections according to the present invention

The warming device may further be configured to accommodate needleless injections as illustrated in FIG. 6. Specifically, device 3 includes a warmer unit 4 and a fitting 21. The warmer unit is substantially similar to the warmer unit described above and includes an IV tube 8 disposed within heat transfer tube 6 and distal and proximal end caps 10, 12. The area between the IV and heat transfer tubes receives a warming or heat transfer fluid, while IV tube 8 contains intravenous fluid for the patient as described above. The IV and heat transfer tubes are connected by walls that partition the area into channels for directing heat transfer fluid flow through the warmer unit in substantially the same manner described above. Distal end cap 10 disposed at the warmer unit distal end is coupled to IV line portion 11 extending to the patient. The distal end cap enables IV fluid to flow from IV tube 8 to IV line portion 11 and directs heat transfer fluid between the channels as described above. Proximal end cap 12 is disposed at the warmer unit proximal end and includes heat transfer fluid inlet 13 and outlet 14. The proximal end cap facilitates flow of heat transfer fluid to and from a heated fluid supply source and through the appropriate channels as described above. The proximal end cap further enables IV fluid to flow into the IV tube from fitting 21 as described above.

Fitting 21 is similar to fitting 20 described above for FIG. 1 and includes generally cylindrical base 70 with a substantially cylindrical projection 72. The projection extends from a base distal portion and is typically oriented at an approximate forty-five degree angle relative to a base longitudinal axis. The projection is connected to IV line portion 28 that extends to an IV fluid source. The line portion typically includes female Luer connector 76 disposed at the line proximal end to facilitate connection of the line to the fluid source. The base proximal portion includes injection site 59 to enable injection of medicaments or other fluids into the IV line. The injection site is similar to the injection site described above and includes membrane 58 to seal the base proximal end and maintain fluids within the fitting.

As described above, syringes typically include needles that may contact and rupture IV tube 8, thereby compromising sterility of the IV fluid and/or contaminating a medical procedure. In order to ensure sterility of the IV fluid, fitting 21 is configured to accommodate a needleless connector 82 in order to facilitate needleless injections. In particular, base 70 includes a connection member 74 extending proximally from membrane 58 of injection site 59. The connection member is substantially cylindrical with a hollow interior and substantially the same width dimension as base 70. The connection member is configured in the form of a female Luer connector and includes fins 78 angularly spaced apart by approximately one-hundred eighty degrees to facilitate connection with needleless connector 82. Basically, needleless connector 82 includes a seal or valve mechanism to enable entry and flow of fluid therethrough from an instrument 79. The instrument is preferably a conventional syringe without a needle containing a medicament or other fluid and including a substantially blunt distal end projection 80 serving as a fluid outlet. The blunt projection generally includes a seal to maintain the fluid in the instrument. Connector 82 further includes a proximal entry site 84 for receiving instrument 79 and a distal end 86 preferably in the form of a male Luer connector for engagement with the female Luer configuration of connection member 74.

The instrument projection is inserted into the needleless connector to facilitate an injection. This penetrates the instrument distal end seal and further enables the needleless connector valve or seal mechanism to permit fluid to flow from the instrument and through the needleless connector. The fluid flows from the needleless connector through membrane 58 and mixes with the IV fluid in base 70. The mixture subsequently flows through warmer unit 4 and to the patient as described above. Removal of the instrument permits the instrument seal to close and disables the valve, thereby maintaining the intravenous fluid and medicament in the fitting and instrument, respectively. The needleless connector may be implemented by any conventional needleless connector, such as the KippMed Needleless Access Connector available from Porex Medical Products, Inc. of Ontario, Calif. For further examples of needleless connectors and systems, reference is made to U.S. Pat. Nos. 5,573,516 (Tyner), 6,146,362 (Turnbull et al.) and 6,344,033 (Jepson et al.), the disclosures of which are incorporated herein by reference in their entireties.

In operation, needleless connector 82 is attached to connector member 74. IV fluid is directed from an IV fluid source through IV line portion 28 to projection 72 of fitting 21. The IV fluid continues traveling through the fitting emerging at the base distal end and passing through proximal end cap 12 into IV tube 8 of warmer unit 4. Heat transfer fluid is continuously circulated through the warmer unit via inlet 13, outlet 14 and channels 36, 38 as described above. The fluid flows from a heat transfer fluid supply source and through warmer unit 4 to surround IV tube 8 and heat fluid flowing therein. The IV fluid passes through the IV tube and exits the warmer unit through distal end cap 10 into IV line portion 11 that extends to the infusion site. Medical instrument 79 containing a medicament or other fluid may be inserted into needleless connector 82 to inject medicaments into the IV line. The instrument distal end is received in the needleless connector to enable medication to flow from the instrument through the needleless connector and into the fitting. The medication mixes with the IV fluid flowing within fitting 21 and flows toward the infusion site as described above. The needleless connector facilitates needleless injection of the medication into the IV line, thereby preventing rupturing of the IV tube.

It will be appreciated that the embodiments described above and illustrated in the drawings represent only a few of the many ways of implementing a method and apparatus for facilitating injection of medication into an intravenous fluid line while maintaining sterility of infused fluids.

The warmer unit of the systems may be of any shape, size and/or configuration, and may be constructed of any suitable materials. The warmer unit may control the temperature of IV or other fluid flowing within the fluid line to any desired temperature or temperature ranges. The systems may include any quantity of warmer units disposed at any locations along the fluid line to heat the fluid. The systems may be utilized with any type of infused or other fluid (e.g., IV, saline, blood, drugs, etc.) from any desired fluid supply source (e.g., bag, container, pump, etc.). The systems may alternatively utilize any type of heat transfer system employing heat transfer fluid for maintaining IV fluids flowing within an IV line at selected temperatures. The warming systems may include any suitable configuration and may include any number of fittings, piping conduits, extension pieces, or other components arranged in any suitable orientation and order with respect to each other for providing a fluid flow path between a fluid supply source and the warmer unit.

The warmer unit may include any quantity of fluid lines coupled to the unit in any desired fashion. The lines may be of any size or shape and may be coupled to the unit or end caps via any conventional or other connectors. The heat transfer and IV tubes and end caps of the warmer unit may be of any shape or size and may be constructed of any desired materials. The tubes may be nested or arranged in any desired fashion. The heat transfer tube may include or be partitioned into any quantity of channels or passages of any shape or size to direct heat transfer fluid in any desired direction. The channels may be disposed within the heat transfer tube at any locations and in any manner. The heat transfer fluid may be implemented by any fluid capable of heating the IV tube and fluid flowing therein (e.g., water or other liquid, gas, etc.).

The end caps may be of any quantity, shape or size and disposed at any suitable locations. The end cap components (e.g., members, conduit, projection, etc.) may be of any quantity, shape or size, may be constructed of any suitable materials and may be arranged or disposed in any fashion. The end caps may include any conventional or other connectors to couple to the fluid line or fitting. The end caps may direct fluid within or into the warming unit in any desired fashion. The end cap walls and chambers may be of any quantity, shape or size, and may be disposed at any location or arranged in any fashion. The heat transfer fluid inlet and outlet may be of any quantity, shape or size and may be disposed at any suitable locations. The heat transfer fluid may be supplied by any suitable source and may be directed through the warmer unit continuously or at any desired intervals or rates to heat the intravenous fluid.

The fittings of the warming devices may be of any quantity, shape or size and may be disposed at any suitable locations with respect to the warmer unit or fluid line. The fittings may be implemented by any types of fittings including any configuration (e.g., tee fittings, cross fittings, elbows, couplings and any combinations thereof, etc.). The fitting components (e.g., base, projection, injection safety member, injection site, etc.) may be of any quantity, shape or size, may be constructed of any suitable materials (e.g., plastic, etc.) and may be disposed at any suitable locations or arranged in any fashion. The projection of the fittings may be oriented at any desired angle relative to the corresponding projection base.

The injection site of the fittings may be of any quantity, shape or size, may be constructed of any desired materials and may be disposed at any suitable locations with respect to the fitting and fluid line. The injection site membrane may be of any quantity, shape or size, may be disposed at any location within the fittings and may be constructed of rubber or any other suitable material. The membrane may be configured as a plug, end cap or any other suitable device capable of sealing an opening at any suitable locations along the fluid line, while permitting a syringe needle or other instrument to be removably inserted through the membrane. The injection safety member may be of any quantity, shape or size, may be constructed of any suitable materials, and may be disposed at any location on the fittings. The injection safety member may accommodate any type of instrument at any location for injection of medication or other fluids (e.g., syringe, etc.) and may be configured in any manner (e.g., partially or fully open end, partially or fully closed end, openings at any locations, etc.) to receive the instrument. The injection safety member may include any desired length and width dimensions to prevent needles or instruments from rupturing the IV tube. The safety member may be attached to the injection site branch of a fitting via any suitable connectors or be formed integral with that branch. Alternatively, the fitting injection site branch may include elongated dimensions sufficient to maintain the syringe needle within the fitting, or may include a membrane or other cover or seal disposed at the proximal end of the safety member. The injection sites may accommodate injection of any types of fluids (e.g., medication, drugs, etc.).

The fitting assembly of the plural fitting embodiment may include any quantity of fittings of any shape or size, disposed at any suitable locations and coupled in any desired fashion. The fittings may be of any quantity, shape or size and may be disposed at any suitable locations with respect to the warmer unit or fluid line. The fittings may be implemented by any types of fittings including any configuration (e.g., tee fittings, cross fittings, elbows, couplings and any combinations thereof, etc.). The fitting components (e.g., base, projection, injection site, etc.) may be of any quantity, shape or size, may be constructed of any suitable materials (e.g., plastic, etc.) and may be disposed at any suitable locations or arranged in any fashion. The projection of the fittings may be oriented at any desired angle relative to the corresponding projection base. The injection site of the fittings may be of any quantity, shape or size, may be constructed of any desired materials and may be disposed at any suitable locations with respect to the fitting and fluid line. The membranes of the injection sites may be of any quantity, shape or size, may be disposed at any location within the fittings and may be constructed of rubber or any other suitable material. The membranes may be configured as a plug, end cap or any other suitable device capable of sealing an opening at any suitable locations along the fluid line, while permitting a syringe needle or other instrument to be removably inserted through the membrane. The fittings may optionally include the injection safety member described above. The fitting assembly may be disposed at any suitable location along the fluid line, and any quantity of injection sites may include the injection safety member and/or be utilized to accommodate injections.

The warming devices may include any quantity of any conventional or other connectors or fasteners to couple the warmer unit, lines, tubes, fittings and fluid supply sources in any fashion. The warming device components (e.g., warmer unit, fittings, etc.) may be formed integral as a single unit or be attached together in any desired fashion (e.g., connectors, welded, etc.).

The needleless warming device fitting may be of any quantity, shape or size and may be disposed at any suitable locations with respect to the warmer unit or fluid line. The fitting may be implemented by any types of fittings including any configuration (e.g., tee fittings, cross fittings, elbows, couplings and any combinations thereof, etc.). The fitting components (e.g., base, projection, injection site, etc.) may be of any quantity, shape or size, may be constructed of any suitable materials (e.g., plastic, etc.) and may be disposed at any suitable locations or arranged in any fashion. The projection of the fitting may be oriented at any desired angle relative to the projection base. The injection site of the fitting may be of any quantity, shape or size, may be constructed of any desired materials and may be disposed at any suitable locations with respect to the fitting and fluid line. The injection site membrane may be of any quantity, shape or size, may be disposed at any location within the fitting and may be constructed of rubber or any other suitable material. The membrane may be configured as a plug, end cap or any other suitable device. The fitting projection may be configured or include any type of connector for engagement with a needleless connector. The needleless connector may be implemented by any conventional or other connector facilitating needless injections, and may include any type of connector for engagement with the projection. The fitting connector may include any quantity of fins or other projections of any shape or size to engage the needleless connector. The needless connector may accommodate any needleless syringe or any other instrument containing fluid for injection into the fluid line. The fitting may optionally function without the membrane and rely on the needleless connector to seal the fitting.

The systems may be utilized individually or be combined in any desired fashion. For example, the plural fitting embodiment may utilize any of the fittings of the other devices (e.g., needleless fitting, fitting with safety member, etc.). Further, any quantity of the devices in any desired combination may be utilized along a fluid line. In addition, the systems (e.g., safety member, plural fitting, needleless, etc.) may be utilized to prevent contact and rupture of any or each of the tubes (e.g., tube carrying intravenous fluid, tube or channels carrying heat transfer fluid, etc.).

It is to be understood that the terms "top", "bottom", "length", "width", "upper", "lower", "horizontal", "vertical", "side" and the like are used herein merely to describe points of reference and do not limit the present invention to any specific configuration or orientation.

From the foregoing description, it will be appreciated that the invention makes available a novel method and apparatus for facilitating injection of medication into an intravenous fluid line while maintaining sterility of infused fluids, wherein an injection site of an infused fluid warming device is configured to prevent rupture of a device IV fluid line during injections of medication into the infused fluid.

Having described preferred embodiments of a new and improved method and apparatus for facilitating injection of medication into an intravenous fluid line while maintaining sterility of infused fluids, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. An infusion system to deliver intravenous fluid from a supply source to an infusion site via a fluid line and to enable injection of medicinal fluid into said fluid line while maintaining sterility of said intravenous fluid, said system comprising:
    a heat transfer unit including first and second conduits, wherein said first conduit receives said intravenous fluid and is connected with a fluid line portion extending toward said infusion site and said second conduit receives heat transfer fluid to heat said intravenous fluid flowing through said first conduit; and
    a fluid connector assembly to facilitate fluid flow between said supply source and said heat transfer unit and including:
        a fitting including a housing structure to receive said intravenous fluid and to direct said intravenous fluid received by said fitting into said heat transfer unit, wherein said housing structure includes:
            an elongated tubular body including a proximal end portion;
            a fluid inlet member with a distal end directly attached to said elongated tubular body and a proximal end to receive intravenous fluid into said housing structure; and
            a fluid outlet disposed at a distal end of said elongated tubular body and secured to said heat transfer unit with said fluid outlet in fluid communication with said first conduit;
        wherein said proximal end portion of said elongated tubular body includes:
            an instrument member positioned within a proximal portion of said elongated tubular body, wherein said instrument member includes a membrane to maintain a fluid tight seal and permit removable insertion of a portion of an instrument through said membrane and within said fluid connector assembly, wherein said instrument includes a syringe containing a medicinal fluid and said instrument portion includes a needle with a length dimension, and wherein said syringe facilitates injection of a medicinal fluid different than said intravenous fluid into said fluid connector assembly; and
            an extension member extending proximally from said instrument member and forming a proximal end of said elongated tubular body, wherein said extension member is configured to engage a syringe distal portion and enable insertion of said needle within said extension member, and wherein said extension member is configured to displace said syringe from said instrument member and provide a distance from said conduits greater than said length dimension of said needle to prevent contact and rupture of said conduits by said needle during said injection.

2. The system of claim 1, wherein said extension member is disposed proximate said membrane and configured to engage said syringe distal portion and displace that portion from said membrane to restrict insertion of said needle into said fluid connector assembly.

3. The system of claim 2, wherein said extension member includes a length dimension in the approximate range of 0.5 to 1.0 inches to distance said needle from said conduits and restrict insertion of said needle into said instrument member.

4. The system of claim 1, wherein said fluid connector assembly further includes:
    a second fitting including:
        a distal end in fluid communication with said fluid inlet member;
        a second fluid inlet member disposed at a proximal end of said second fitting to receive said intravenous fluid from said supply source; and
        a second proximal end in the form of an entry site to facilitate injection of said medicinal fluid into said second fitting via said needle.

5. In an infusion system to deliver intravenous fluid from a supply source to an infusion site via a fluid line including a heat transfer unit including first and second conduits, wherein said first conduit receives said intravenous fluid and said second conduit receives heat transfer fluid to heat said intravenous fluid, and a fluid connector assembly to facilitate fluid flow between said supply source and said heat transfer unit, a method of injecting medicinal fluid into said fluid line while maintaining sterility of said intravenous fluid comprising:
    (a) receiving said intravenous fluid from said supply source within a fitting of said fluid connector assembly and directing said intravenous fluid received by said fitting from said supply source into said heat transfer unit, wherein said fitting includes a housing structure including an elongated tubular body with a proximal end portion, a fluid inlet member with a distal end directly attached to said elongated tubular body and a proximal end to receive intravenous fluid into said housing structure, and a fluid outlet disposed at a distal end of said elongated tubular body and secured to said heat transfer unit with said fluid outlet in fluid communication with said first conduit, wherein said proximal end portion of said elongated tubular body includes an instrument member positioned within a proximal portion of said elongated tubular body and an extension member extending proximally from said instrument member and forming a proximal end of said elongated tubular body, and wherein said instrument member includes a membrane to maintain a fluid tight seal and permit removable insertion of a portion of an instrument through said membrane and within said fluid connector assembly;

(b) receiving said instrument portion within said instrument member to facilitate injection of a medicinal fluid different than said intravenous fluid into said fluid connector assembly, wherein said instrument includes a syringe containing said medicinal fluid and said instrument portion includes a needle with a length dimension; and (c) engaging a syringe distal portion via said extension member and displacing said syringe from said instrument member and providing a distance from said conduits greater than said length dimension of said needle to prevent contact and rupture of said conduits by said needle during said injection.

6. The method of claim 5, wherein step (c) further includes:

(c.1) engaging said syringe distal portion, via said extension member disposed proximate said membrane, and displacing that portion from said membrane to limit insertion of said needle into said fluid connector assembly.

7. The method of claim 6, wherein said extension member includes a length dimension in the approximate range of 0.5 to 1.0 inches, and step (c.1) further includes:

(c.1.1) displacing said needle from said conduits by restricting insertion of said needle into said instrument member via said extension member.

8. The method of claim 5, wherein said fluid connector assembly further includes a second fitting including a distal end in fluid communication with said fluid inlet member, a second fluid inlet member disposed at a proximal end of said second fitting to receive intravenous fluid, and a second proximal end in the form of an entry site to facilitate injection of said medicinal fluid into said second fitting via said needle, and step (c) further includes:

(c.1) displacing said received needle from said conduits by receiving said needle within said entry site of said second fitting.

9. An infusion system to deliver intravenous fluid from a supply source to an infusion site via a fluid line and to enable injection of medicinal fluid into said fluid line while maintaining sterility of said intravenous fluid, said system comprising:

heating means for heating said intravenous fluid and including first and second conduits, wherein said first conduit receives said intravenous fluid and is connected with a fluid line portion extending toward said infusion site and said second conduit receives heat transfer fluid to heat said intravenous fluid flowing through said first conduit; and fluid connection means for facilitating fluid flow between said supply source and said heating means and including:

flow means including a housing structure for receiving said intravenous fluid and directing said intravenous fluid received by said flow means into said heating means, wherein said housing structure includes:

an elongated tubular body including a proximal end portion;

fluid inlet means with a distal end directly attached to said elongated tubular body and a proximal end to receive intravenous fluid into said housing structure; and fluid outlet means disposed at a distal end of said elongated tubular body and secured to said heating means with said fluid outlet means in fluid communication with said first conduit;

wherein said proximal end portion of said elongated tubular body includes:

instrument means positioned within a proximal portion of said elongated tubular body, wherein said instrument means includes a membrane to maintain a fluid tight seal and permit removable insertion of a portion of an instrument through said membrane and within said fluid connection means, wherein said instrument includes a syringe containing a medicinal fluid and said instrument portion includes a needle with a length dimension, and wherein said syringe facilitates injection of a medicinal fluid different than said intravenous fluid into said fluid connection means; and extension means extending proximally from said instrument means and forming a proximal end of said elongated tubular body, wherein said extension means is configured to engage a syringe distal portion and enable insertion of said needle within said extension means, and wherein said extension means displaces said syringe from said instrument means and provides a distance from said conduits greater than said length dimension of said needle to prevent contact and rupture of said conduits by said needle during said injection.

10. The system of claim 9, wherein said extension means is disposed proximate said membrane and configured to engage said syringe distal portion and displace that portion from said membrane to restrict insertion of said needle into said fluid connection means.

11. The system of claim 10, wherein said extension means includes a length dimension in the approximate range of 0.5 to 1.0 inches to distance said needle from said conduits and restrict insertion of said needle into said instrument means.

12. The system of claim 9, wherein said fluid connection means further includes:

second flow means including:

a distal end in fluid communication with said fluid inlet means;

second fluid inlet means disposed at a proximal end of said second flow means to receive said intravenous fluid from said supply source; and a second proximal end in the form of an entry site to facilitate injection of said medicinal fluid into said second flow means via said needle.

* * * * *